United States Patent
Suzuki et al.

(10) Patent No.: US 6,742,660 B2
(45) Date of Patent: Jun. 1, 2004

(54) ANTIBACTERIAL AND BIODEGRADABLE EXTRACTING CONTAINER

(75) Inventors: Kaichi Suzuki, Kyoto (JP); Kouji Kajiwara, Fujieda (JP); Shuhei Kurata, Osaka (JP)

(73) Assignees: Yamanaka Ind., Kyoto (JP); Unitika Fibers, Ltd., Osaka (JP)

( * ) Notice: Subject to any disclaimer, the term of this patent is extended or adjusted under 35 U.S.C. 154(b) by 75 days.

(21) Appl. No.: 10/169,599

(22) PCT Filed: Dec. 11, 2000

(86) PCT No.: PCT/JP00/08752

§ 371 (c)(1),
(2), (4) Date: Sep. 16, 2002

(87) PCT Pub. No.: WO01/49584

PCT Pub. Date: Jul. 12, 2001

(65) Prior Publication Data

US 2003/0099791 A1 May 29, 2003

(30) Foreign Application Priority Data

Jan. 6, 2000 (JP) ........................................ 2000-005784

(51) Int. Cl.[7] .................. B01D 29/00; B01D 39/08; B65D 77/00; A23F 3/16; A23F 5/26

(52) U.S. Cl. .................. 210/505; 210/501; 210/503; 426/321; 428/34.1; 428/35.7; 428/36.1

(58) Field of Search ................................ 210/501, 503, 210/505, 507, 500.1, 416.3; 426/321; 428/34.1, 34.5, 35.7, 36.1; 524/109, 114; 604/408

(56) References Cited

U.S. PATENT DOCUMENTS

| | | | |
|---|---|---|---|
| 2,046,334 A | 7/1936 | Loeber |
| 2,624,489 A | 1/1953 | Wishart |
| 2,860,858 A | 11/1958 | Kurs |
| 2,900,656 A | 8/1959 | Tupper |
| D188,593 S | 8/1960 | Tegarty |
| 3,411,723 A | 11/1968 | Kohn |
| 3,450,319 A | 6/1969 | Ray et al. |
| 4,350,445 A | 9/1982 | Olsson |
| 4,405,067 A | 9/1983 | Caron |
| 4,570,838 A | 2/1986 | Szemere et al. |
| 5,054,338 A | 10/1991 | Weis |
| 5,103,520 A | 4/1992 | Mazzo |
| 5,498,650 A | 3/1996 | Flexman et al. |
| 5,549,380 A | 8/1996 | Lidgren et al. |
| 5,875,515 A | 3/1999 | Dallas |
| 6,244,487 B1 | 6/2001 | Murray |
| 6,247,736 B1 | 6/2001 | Esterson et al. |
| 6,257,474 B1 | 7/2001 | Jones et al. |

FOREIGN PATENT DOCUMENTS

| | | |
|---|---|---|
| JP | 4-334448 | 11/1992 |
| JP | 7-310236 | 11/1995 |
| JP | 11-42164 | 2/1999 |

OTHER PUBLICATIONS

Internal Search Report of PCT/JP00/08752, dated Mar. 13, 2001.

Internal Preliminary Examination Report of PCT/JP00/08757, dated Aug. 6, 2001.

*Primary Examiner*—John Kim
(74) *Attorney, Agent, or Firm*—Christie, Parker & Hale, LLP

(57) ABSTRACT

An antibacterial, biodegradable extracting container has a filtering surface formed from a water-permeable woven or knitted fabric formed from fibers comprising, as a principal component, an antibacterial, biodegradable polylactate polymer, and having a thickness of 1 to 100 dtex, wherein, preferably, the filtering surface is formed from the woven fabric having a cover factor K of 1600 to 6400, determined in accordance the following equation:

$$K = (N \times (A)^{1/2}/T) + (M \times (B)^{1/2}/S)$$

wherein, N=warp density (yarns/10 cm), M=weft density (yarns/10 cm), A=thickness (dtex) of the warp yarns, B=thickness (dtex) of the weft yarns, T=specific gravity of the warp yarns and S=specific gravity of the weft yarns.

2 Claims, No Drawings

ANTIBACTERIAL AND BIODEGRADABLE EXTRACTING CONTAINER

CROSS-REFERENCE TO RELATED APPLICATION

This application claims priority of International application number PCT/JP00/08752, filed Dec. 11, 2000, which in turn claims priority of Japanese application number 2000/5784, filed Jan. 6, 2000.

TECHNICAL FIELD

The present invention relates to a biodegradable extracting container. More particularly, the present invention relates to a biodegradable extracting container for extracting a drink material, for example, coffee, black tea, green tea, or oolong tea, with hot water or cold water.

BACKGROUND ART

In conventional extracting bags for extracting a drink material, for example, coffee, black tea, green tea or oolong tea with hot water or cold water, the bags are usually formed from woven fabrics, nonwoven fabrics comprising synthetic fibers selected from, for example, nylon filaments and polyester filaments, or paper sheets.

After the synthetic fiber bags are used to extract the drink material such as tea, the used bags are discharged as home waste. In this case, as the synthetic fibers from which the bags are formed, per se have no biodegrability, the used bags are necessarily sent to a reclaiming treatment or to a burning and then reclaiming treatment, and this necessity causes an increase in the amount of wastes which is currently a social problem.

Compared with the synthetic fiber bags, the paper bags exhibits a biodegradability and thus the discharge of the used paper bags does not cause the above-mentioned problems.

When the drink material is contained in a bag formed from conventional synthetic fibers or paper sheets, and stored in storing surroundings having a high humidity and a high temperature, the problem such that in the contained material in the bag, various molds and bacteria grow thereon due to non-antibacterial property of the bag itself. In the prior art, to solve the above-mentioned problem, the bag is covered with a non-gas-permeable sheet by which the bag is protected from moisture.

For this covering, complicated and costly procedures are needed.

It is known that the anti-bacterial property can be imparted to the synthetic fibers by knead-mixing an antibacterial agent into a fiber-forming material during filament-forming procedures, or fixing the antibacterial agent on the surfaces of the filaments made by the filament-forming procedures with a resinous binder. The above-mentioned application of the anti-bacterial agent to the synthetic fibers are not appropriately in view of the possibility of such an occurrence that the antibacterial agent is extracted into hot water or cold water during an extracting procedure, and the fragrance and safety of the extracted drink are degraded.

Also, before the used extracting bag is discarded as a waste, the extraction residue in the bag is retained in a water-holding condition. During this stage, as the conventional fiber bag has no antibacterial property, various bacteria and molds are grown on portions of the residual material contacting with water, and a slimy substance and an offensive odor are generated. Therefor, when the used bag is discharged as waste, a strong offensive odor is felt and a discharging operation becomes difficult. Particularly, in the summer season, the bacteria vigorously propagate and, thus, there is a possibility of occurrence of poisoning through hands brought into contact with the waste.

As stated above, the extracting bag formed from the conventional synthetic fibers does not exhibit a biodegrading property and, therefore, when tea leaves contained and sealed in an extracting bag are stored, for the purpose of inhibiting the propagation of the various mold and bacteria, the extracting bag is packaged with a water-proof sheet. However, the above-mentioned packaging is disadvantageous in that complicated and costly procedures are needed. Also, in this case, before the extracting bag is used, a procedure of removing the packaging sheet from the bag is needed, and the removed packaging sheet which is completely unnecessary for the extraction using the extracting bag must be discharging. Namely, the use of the packaging sheet is disadvantageous in that a discharging procedure is needed and a waste is generated.

Also, with respect to the treatment of the used drink-extracting bags, it should be noted that, as the conventional synthetic fiber bags do not have biodegradability, the used bag waste must be sent to a reclaiming treatment or a burning and then reclaiming treatment. This necessity causes an increase in the amount of waste.

Also, the conventional extracting bags formed from the synthetic fibers are disadvantageous in that various bacteria and molds propagate on the extraction residue in the used bags so as to cause slimy substances and offensive odor are generated, and there is a possibility of occurrence of poisoning through the hands contacting the used bags.

SUMMARY OF THE INVENTION

An object of the present invention is to provide an antibacterial, biodegradable extracting container formed from an extract-filtering material which can prevent propagation of bacteria and mold on the material contained in the container and to be subjected to extraction, and which, per se, is bio-degradable.

The antibacterial, bio-degradable extracting container of the present invention has a filtering surface formed from a water-permeable sheet selected from woven and knitted fabrics, and is characterized in that fibers from which the water-permeable sheet is formed comprises, as a principal component, an antibacterial, biodegradable polylactate polymer, and have a thickness of 1 to 100 dtex.

In the antibacterial, biodegradable extracting container of the present invention, the filtering surface may form at least a portion of surfaces of a bag-formed container.

In the antibacterial, biodegradable extracting container of the present invention, the water-permeable fabric sheet from which the filtering surface is formed preferably has a cover factor K of 1600 to 6400, determined in accordance with the following equation:

$$K=(N\times(A)^{1/2}/T)+(M\times(B)^{1/2}/S)$$

wherein, N represents a warp density (yarns/10 cm), M represents a weft density (yarns/10 cm), A represents a thickness (dtex) of the warp yarns, B represents a thickness (dtex) of the waft yarns, T represents a specific gravity of the warp yarns and S represents a specific gravity of the weft yarns.

BEST MODE OF CARRYING OUT THE INVENTION

The filtering surface of the antibacterial, biodegradable extracting container of the present invention is formed from a water-permeable sheet selected from water-permeable woven and knitted fabrics formed from fibers comprising an antibacterial, biodegradable polylactate polymer and having a thickness of 1 to 100 dtex.

In the present invention, the term "antibacterial property" refers to a characteristic of preventing propagation of bacteria and molds on a material contained in the extracting container of the present invention and to be subjected to extraction, namely, coffee particles or various types of tea leaves.

Namely, the extracting container of the present invention has a characteristic of controlling the propagation of bacteria and molds and exhibits a bactericidal activity value of O or more. The bactericidal activity value is a parameter representing an antibacterial property, determined in JIS L 1902. When the bactericidal activity value is less than 0, the bacteria can propagate and thus the object of the present invention cannot be attained.

The antibacterial, biodegradable extracting container of the present invention has a filtering surface through which an extract solution obtained by extracting the material contained in the container and to be extracted with cold water or hot water, is filtered. The filtering surface is formed from a water-permeable sheet selected from woven and knitted fabrics. The fibers from which the woven and knitted fabrics are formed comprises, as a principal component, an antibacterial, biodegradable polylactate polymer, and has a thickness of 1 to 100 dtex. Preferably, 50% by weight or more of the fibers from which the filtering surface of the water-permeable sheet are formed from the antibacterial, biodegradable polylactate polymer. More preferably, 100% by weight of the filtering surface-forming fibers are formed from the polylactate polymer.

The polylactate polymer usable for the present invention is one prepared by polymerizing lactic acid or dimer lactide of lactic acid which is used as a monomer. The polymer may be selected from homopolymers of optical isomers D and L, copolymers of the optical isomers D and L with each other or a mixture of the homopolymers and the copolymers.

For the purpose of imparting an antibacterial property to the extracting container, the inventors of the present invention carried out an extensive study on various polymers, and, as a result, found that the above-mentioned polylactate polymer exhibits an excellent antibacterial property and is optimum as a material for forming the extracting container.

The fibers comprising, as a principle component, preferably in a content of 50% by weight or more, the polylactate polymer may be in the form of multifilaments, monofilaments or staple fibers. The staple fibers may be employed in the form of spun yarns, or in the form of composite yarns comprising the staple fibers and the filaments. There is no limitation to the cross-sectional profile of the fibers and filaments. Usually, a circular cross-sectional profile is preferred. In consideration of the meaning and knitting property of the fibers, the flexibility and extracting property of the container (bag), extracting property of the container and degree of filter leakage of the extract in the container, the thickness of the polylactate polymer fibers must be in the range of from 1 to 100 dtex, preferably 5 to 50 dtex.

If the thickness is less than one dtex, while the resultant water-permeable sheet exhibit a satisfactory flexibility, in the water-permeable sheet selected from the woven and knitted fabrics, slippage of the yarns easily occurs, and when the woven or knitted fabric is constituted in an increased yarn density, the weaving and knitting efficiency is decreased, and the resultant fabric is disadvantageous in that in the extracting procedure, clogging of the filtering surface occurs and the filtering efficiency becomes unsatisfactory. Also, if the thickness is more than 100 dtex, the resultant water-permeable woven or knitted fabric exhibit an increased stiffness and an insufficient flexibility, and when the weaving or knitting density is decreased for the purpose of increasing the flexibility of the fabric, the resultant fabric has large gaps between the yarns, and allows the solid fraction in the container to leak through the filtering fabric surface during the extracting procedure, namely, a disadvantageous filter leaking phenomenon occurs.

In the case where, in the extracting container of the present invention, the water-permeable sheet produced from the polylactate polymer fibers is a woven fabric, the cover factor K is preferably 1600 to 6400, more preferably 3200 to 4000. The cover factor K is determined in accordance with the following equation.

$$K=(N\times(A)^{1/2}/T)+(M\times(B)^{1/2}/S)$$

wherein, K represents a cover factor of the woven fabric, N represents a warp density (yarns/10 cm), M represents a weft density (yarns/10 cm), A represents a thickness (dtex) of the warp yarns, B represents a thickness (dtex) of the weft yarns, T represents a specific gravity of the warp yarns and S represents a specific gravity of the weft yarns, of the woven fabric. If the cover factor K of the woven fabric for the water-permeable sheet is less than 1600, the filter leak in the extraction may be too much, and if the cover factor K is more than 6400, the clogging of the filtering surface may occur during the extraction.

In the extracting container of the present invention, there is no limitation to the form and dimensions thereof, as long as the container is provided with at least one filtering surface formed from the water-permeable sheet as specified above. The container may be a bag-formed container (bag) formed from the specific water-permeable sheet. The bag-formed container may be a extracting bag having only front and back filtering surfaces, or another extracting bag having front and back filtering surfaces, right and left side gore filtering surfaces and a bottom gore filtering surface. Further the extracting container may be in the form of a polyhedron, for example, a tetrahedron or hexahedron (box-form), or a cylinder. In this case, the polyhydronal or cylindrical container must be provided with at least one extracting surface formed from the water-permeable sheet specified in the present invention. Alternatively, the extracting container of the present invention may be provided with, in addition to the bag-formed container formed from the specific water-permeable sheet, a supporting member of the bag-formed container.

Where the extracting container of the present invention is an extracting bag, the bag is produced by cutting the specific water permeable sheet into a desired size, the cut sheet is folded double and two side edges are bound by a heat melt-welding method or high frequency welding method or ultrasonic welding method to form a bag, while a top edge is maintained open, to provide an inlet for feeding a material to be extracted into the resultant bag. The material to be extracted is placed into the bag, and the open top edge of the bag is sealed by the above-mentioned welding method. The extracting container in another form can be produced by using the specific water-permeable sheet as defined in the present invention by a conventional container-producing method.

A hanging member attached to the extracting bag comprises a hanging thread comprising, for example, twisted multifilament or monofilament yarn or a spun yarn of staple fibers and a tag made from a sheet material, for example, a paper sheet, and connected to a top end of the hanging thread. Preferably, the hanging thread and the tag are produced from a biodegradable material, for example, polylactate polymer or cellulose, to enable the hanging member attached to the extracting bag to be completely biodegraded.

The water-permeable sheet from which the filtering surface of the extracting container of the present invention is produced from synthetic fibers comprising, as a principal component, a polylactate polymer. When the material to be extracted, for example, coffee particles or tea leaves, is wetted with water, or after the extraction is completed, the polylactate polymer fibers in the filtering surface exhibit a performance of preventing the propagation of the bacteria and molds adhered to the wetted extracted material, and after the used extracting container is discarded, the polylactate polymer fibers are biodegraded. Also, as the polylactate polymer has a melt-bonding property, the polylactate polymer fiber sheet can be melt-bonded by the conventional heat welding method, high frequency welding method, and ultrasonic welding method. Accordingly, the extracting container of the present invention enables the material to be extracted, contained in the container, to be maintained fresh during storage thereof without packaging the material with a non-gas-permeable material, and after using, the propagation of saprogens, for example, staphylococcus aureus and pseudomonas aeruginosa, and molds and the generation of putrid odor and slimy substance. Also, when the extracting container is discarded after use, the container is biodegraded by degradation bacteria in the earth and disappears. Namely, the polylactate polymer is hydrolysed to split the molecular chains thereof in the initial stage of the biodegradation. The hydrolysis is carried out at an accelated rate under high temperature and high humidity conditions, and at a low rate at room temperature. After the splitting of the polymeric molecular chains has progressed to a certain extent, the hydrolysis product is further decomposed by the action of the natural degradation bacteria, for example, heat-resisting spore bacteria and/or anaerophytes. It is noted that almost of all of the degradation bacteria exist in the earth and few degradation bacteria exist in the air. Thus, the bacteria existing in the air substantially do not degrade the polylactate polymer.

The extracting container of the present invention can be rapidly biodegraded, after use, by using a conventional compost treatment apparatus available on trade. In this case, the compost treatment is usually carried out at a temperature of 45 to 100° C., preferably 50 to 80° C. If the treatment temperature is less than 45° C., not only the degradation rate may be too low, but also propagation of various bacteria other than the degradation bacteria effective on the biodegradation may be promoted and thus the treatment surroundings may become insanitary and the degradation bacteria may be affected by the non-degradation bacteria. If the treatment temperature is more than 100° C., the handling and surroundings may be dangerous in view of prevention of disasters, and/or the degradation bacteria may die out. To adjust the treatment temperature as mentioned above, a heater may be used or for certain types of bacteria, or metabolic heat generated by the degradation bacteria may be utilized.

The degradation bacteria usable for the compost treatment at a relatively high temperature as mentioned above are preferably selected from thermophilic bacteria, for example, bacillus brevis.

EXAMPLES

The present invention will be further illustrated by the following examples.

Example 1

A plain woven fabric having a cover factor K of 3480 was produced from warp and weft yarns each consisting of a poly-L-lactate monofilament having a thickness of 25 dtex and a specific gravity of 1.24, in a warp density of 465 yarns/10 cm and a weft density of 398 yarns/10 cm, scoured and finish-set. The woven fabric in the form of a wound roll was slit into a width of 130 cm and subjected to a cut-sealing procedure by an ultrasonic method to prepare flat bags having dimensions of 65 mm length×42 mm width. Extracting bags of the present invention were obtained.

Example 2

A plain woven fabric having a cover factor K of 3730 was produced from warp and weft yarns each consisting of a poly-L-lactate monofilament having a thickness of 25 dtex and a specific gravity of 1.24, in a warp density of 492 yarns/10 cm and a weft density of 433 yarns/10 cm, scoured and finish-set. The woven fabric in the form of a wound roll was slit into a width of 130 cm and subjected to a cut-sealing procedure by an ultrasonic method to prepare flat bags having dimensions of 65 mm length×42 mm width. Extracting bags of the present invention were obtained.

Comparative Example 1

A plain woven fabric having a cover factor K of 2791 was produced from warp and weft yarns each consisting of a polyester monofilament having a thickness of 28 dtex and a specific gravity of 1.38, in a warp density of 374 yarns/10 cm and a weft density of 354 yarns/10 cm, scoured and finish-set. The woven fabric in the form of a wound roll was slit into a width of 130 cm and subjected to a cut-sealing procedure by an ultrasonic method to prepare flat bags having dimensions of 65 mm length×42 mm width. Comparative extracting bags were obtained.

Comparative Example 2

A plain woven fabric having a cover factor K of 3624 was produced from warp and weft yarns each consisting of a polyester monofilament having a thickness of 28 dtex and a specific gravity of 1.38, in a warp density of 512 yarns/10 cm and a weft density of 433 yarns/10 cm, scoured and finish-set. The woven fabric in the form of a wound roll was slit into a width of 130 cm and subjected to a cut-sealing procedure by an ultrasonic method to prepare flat bags having dimensions of 65 mm length×42 mm width. Comparative extracting bags were obtained.

Comparative Example 3

A comparative extracting bags were produced by the same procedures as in Example 1, except that in the plain woven fabric, the warp density was changed to 213 yarns/10 cm, the weft density was changed to 181 yarns/10 cm and the cover factor K of the fabric was changed to 1589.

Note: In Comparative Examples 1 and 2, the diameter of the polyester filaments was established at the same as that of the polylactate filaments used in Examples 1 and 2.

Tea Leaf-extracting Performance Test

As tea leaves to be contained in the extracting bag, green tea leaves available in the trade were purchased, and sieved into a fraction not passed through a sieve No. 30 and a fraction passed through a sieve No. 50 and the sieve No. 30-not-passed fraction in an amount of 80% by weight was evenly mixed with the sieve No. 50-passed fraction in an amount of 20% by weight, in accordance with Hara and two others, "the measurement method of tea product by standard sieves" CHA GI KEN, No. 11, pages 45 to 49 (1958), to enhance the reproducibility of the filter leak property of fine tea leaves particles and the extracting property. The mixed tea leaves were placed in an amount of 2 g (±5%) weighed by a precision balance in each extracting bag through a top opening of the bag.

In each of Examples 1 and 2 and Comparative Examples 1, 2 and 3, 30 extracting bags containing the tea leaves were prepared, and subjected to measurement and evaluation of the leaking property of fine particles of the tea leaves through the bags, before extraction and after extraction.

The extraction of the tea leaves contained in the extracting bags were carried out in accordance with the standard tea examination method (hot water-extracting method, and the amounts of the fine tea leaf particles leaked through the extracting bags was determined by the following testing method.

The amounts of the fine tea leaf particles leaked through the bags were measured on each of the bags (dry) before extracting and the bags after extracting. In each measurement of the amount of the leaked fine particles before extracting, the bag was shaken 20 times in up-to-down directions within a 300 ml beaker in such a manner that no particles are spattered to the outside of the beaker, to collect the fine particles leaked through the bag in the beaker. The above-mentioned procedures were repeated for another 4 bags in the same beaker, the collected fine, particles were mixed with distilled water, the mixture was filtered through a quantitative filter paper the dry mass of which was measured before the test, the filter paper used was dried, an increase in weight of the filter paper was determined, and from the data, the amount of the leaked fine tea leaf particles per pag was calculated.

Separately, to determine the amount of the fine tea leaf particles leaked through the bag after extracting, the extracted bag was carefully placed on a bottom of 300 ml beaker, 200 ml of hot water boiled for 5 minutes were poured as fast as possible (within 20 seconds) into the beaker, the bag was kept in a calmly sunk condition in the beaker for 5 minutes, thereafter, the bag is taken up as fast as possible from the beaker, the fine particles precipitated in the inside of the beaker was filter-separated through a quantitative filter paper No. 2 the weight of which was determined before the testing, the filter paper was dried in a desiccator, then the mass of the filtered fine particles was determined.

The results are shown in Table 1.

TABLE 1

Amount of fine tea leaf particles leaked through tea bag

| | The number of measurements | Amount of leaked fine particles before extraction (Average, g/bag) | Amount of leaked fine particles after extraction (Average, g/bag) |
|---|---|---|---|
| Example 1 | 5 times | 0.0256 | 0.0699 |
| Example 2 | 5 times | 0.0247 | 0.0645 |
| Comparative Example 1 | 5 times | 0.0292 | 0.0741 |
| Comparative Example 2 | 5 times | 0.0272 | 0.0717 |
| Comparative Example 3 | 5 times | 0.0806 | 0.1088 |

Table 1 clearly shows that in Examples 1 and 2, the amount of the leaked fine particles was small. In Comparative Example 3, however, the amount of the leaked fine particles was large.

The extracting bags used in extraction in Examples 1 and 2 and Comparative Examples 1 and 2 were subjected to the following degradation test in compost.

Biodegradation Test in Compost

In this test, an aging compost treatment apparatus for about 40 days fermentation, made by Nihon Seikosho was employed. The degradation property test was carried out in accordance with ISO/FDIS 14855, and the degradation degree test was carried out in accordance with ISO/CD 16929.

The tea leaves-containing extracting bag after extraction was left on a filter paper under conditions of 25° C. and 65% RH for 24 hours, then was placed in a polyester net and embedded in the compost treatment apparatus. During the test, as a degradation sample, a sample of tea leaves having a size of 1 mm or more, was collected.

The compost treatment was carried out at a compost temperature of 58° C., at a temperature of air of 58° C. passing through the compost treatment apparatus, at a flow rate of air of 600 liters/hour, in a water content in the compost of 60 to 43% at a water vessel temperature of 70° C.

With respect to the degradation property of the extracting bag under the compost treatment conditions, Table 2 shows tensile strength-retention of the bag, Table 3 shows weight reduction of the bag and Table 4 shows molecular weight-retention.

TABLE 2

Degradation property test of tea bag in compost treatment apparatus

| | | Tensile-strength retention (%) | | | | |
|---|---|---|---|---|---|---|
| | | Before treatment | Compost treatment period | | | |
| | | | 3 days | 7 days | 10 days | 14 days |
| Example | 1 | 100 | 40 | 0 | 0 | 0 |
| | 2 | 100 | 43 | 0 | 0 | 0 |
| Comparative | 1 | 100 | 94 | 92 | 91 | 90 |
| Example | 2 | 100 | 93 | 91 | 91 | 91 |

TABLE 3

| | | Weight retention (%) | | | | |
|---|---|---|---|---|---|---|
| | | Before treatment | Compost treatment period | | | |
| | | | 3 days | 7 days | 10 days | 14 days |
| Example | 1 | 100 | 99 | 100 | 57 | 15 |
| | 2 | 100 | 100 | 100 | 60 | 16 |
| Comparative | 1 | 100 | 100 | 100 | 100 | 100 |
| Example | 2 | 100 | 100 | 100 | 100 | 100 |

TABLE 4

| | | Molecular weight retention (%) | | | | |
|---|---|---|---|---|---|---|
| | | Before treatment | Compost treatment period | | | |
| | | | 3 days | 7 days | 10 days | 14 days |
| Example | 1 | 100 | 72 | 39 | 20 | 10 |
| | 2 | 100 | 74 | 40 | 20 | 11 |
| Comparative | 1 | 100 | 100 | 100 | 100 | 100 |
| Example | 2 | 100 | 100 | 100 | 100 | 100 |

In the test results shown in Tables 2 to 4, it was confirmed that the extracting bags of Examples 1 and 2 were biodegraded by the compost treatment. In Comparative Examples 1 and 2, however, the biodegradation of the comparative extracting bags were not confirmed.

Antibacterial Property Test

Each of the extracting bags of Examples 1 and 2 and Comparative Examples 1 and 2 before extraction and after extraction was subjected to an antibacterial test in which the bactericidal activity of the bag was measured in accordance with JIS-L1902, by using, as testing bacteria, Staphylococcus aureus ATCC 6538P and Pseudomonase areuginosa IF03080, to evaluate the antibacterial property of the bag.

From the test results of the extracting bag before extraction, the storage performance of the tea leaves in the bag was evaluated. Also, from the test results of the extracting bag after extraction, the hygienic performance of the extracting bag was evaluated.

Also, the extracting bag after extraction of the tea leaves was left standing on a polyethylene sheet under conditions of 25° C. and 65% RH, and the generation of odor and slimy substance was checked and evaluated. The bactericidal activity test results of the extracting bags before and after extraction are shown in Tables 5 and 6.

TABLE 5

Bactericidal activity test of extracting bag before extraction

| | | Bactericidal activity | |
|---|---|---|---|
| Testing bacteria | | Staphylococcus aureus ATCC 6538P | Pseudomonase areuginosa IF03080 |
| Example | 1 | 2.0 | 1.7 |
| | 2 | 2.5 | 1.9 |
| Comparative Example | 1 | −2.8 | −1.5 |
| | 2 | −2.5 | −1.7 |

TABLE 6

Bactericidal activity test of extracting bag after extraction

| | | Bactericidal activity | |
|---|---|---|---|
| Testing bacteria | | Staphylococcus aureus ATCC 6538P | Pseudomonase areuginosa IF03080 |
| Example | 1 | 1.9 | 1.5 |
| | 2 | 1.9 | 1.6 |
| Comparative Example | 1 | −2.1 | −1.3 |
| | 2 | −2.2 | −1.5 |

In the test results shown in Tables 5 and 6, it was confirmed that the extracting bags of Examples 1 and 2 exhibit an antibacterial property not only before extraction but also after extraction. Also, in the test in which the extracting bags were left standing on the polyethylene sheet, no offensive odor and no slimy substance were generated from and on the extracting bags of Examples 1 and 2 whereas, for the extracting bags of Comparative Examples 1 and 2, a slimy substance was generated on, and an offensive odor was emitted from, the extracting bags.

INDUSTRIAL APPLICABILITY OF THE INVENTION

The extracting container of the present invention using a water-permeable sheet comprising polylactate polymer fibers has a practically sufficient extract-filtering performance, and exhibits excellent biodegradability and a superior antibacterial property to the material contained in the bag, not only before extraction and but also after extraction.

Particularly, in the extracting container of the present invention, the woven or knitted fabric comprising the antibacterial polylactate polymer fibers used to form the container, enables the propagation of molds and bacteria on the material contained in the container and to be extracted to be inhibited to enhance the storage performance of the material to be extracted, such as tea leaves, the generation of offensive odor and slimy substance on the material after extraction to be prevented, and the extracting container to be biodegraded together with the extracted material therein.

What is claimed is:

1. An antibacterial, biodegradable extracting container having a filtering surface formed from a water-permeable sheet selected from woven fabrics, wherein fibers from which the water-permeable sheet is formed comprises, as a principle component, an antibacterial, biodegradable polyactate polymer, and have a thickness of 1 to 100 dtex, and the water-permeable fabric sheet, from which the filtering surface is formed, has a cover factor K of 1600 to 6400 determined in accordance with the following equation;

$$K=(N\times(A)^{1/2}/T)+(M\times(B)^{1/2}/S)$$

wherein, N represents a warp density (yarn/10 cm), M represents a weft density (yarn/10 cm), A represents a thickness (dtex) of the warp yarns, B represents a thickness (dtex) of the weft yarns, T represents a specific gravity of the warp yarn and S represents a specific gravity of the weft yarns.

2. The antibacterial, biodegradable extracting container as claimed in claim 1, wherein the filtering surface forms at least a portion of surfaces of a bag-formed container.

* * * * *

UNITED STATES PATENT AND TRADEMARK OFFICE
CERTIFICATE OF CORRECTION

PATENT NO. : 6,742,660 B2
DATED : June 1, 2004
INVENTOR(S) : Suzuki et al.

It is certified that error appears in the above-identified patent and that said Letters Patent is hereby corrected as shown below:

Title page,
Item [73], Assignees, delete "Yamanaka Ind., Kyoto (JP)" insert --Yamanaka Ind. Co. Ltd., Kyoto (JP) -- and delete "Unitaka Fibers, Ltd.", insert -- Unitaka Fibers Ltd. --
Item [56], References Cited, U.S. PATENT DOCUMENTS,
delete "D188,593 S 8/1960 Tegarty", insert -- D188,593 8/1960 Tegarty --

Column 1,
Line 30, delete "," after "formed"
Line 33, delete "wastes", insert -- waste --
Line 36, delete "exhibits", insert -- exhibit --
Line 41, insert -- is -- after "the problem"
Line 43, insert -- the -- after "due to"
Line 56, delete "are not appropriately", insert -- is not appropriate --
Line 60, delete "a"
Line 66, delete "Therefor", insert -- Therefore --

Column 2,
Line 1, delete "Particularly,", insert -- Particularly --
Line 17, delete "discharging", insert -- discharged --
Line 19, delete "a"
Line 29, delete "as to cause", insert -- that --
Line 37, delete "and to", insert -- which can --
Line 43, delete "comprises", insert -- comprise --
Line 48, delete "surfaces", insert -- the surface --
Line 58, delete "waft", insert -- weft --

Column 3,
Lines 8-10, delete "and to be subjected to extraction, namely, coffee particles or various types of tea leaves", insert -- namely, coffee particles or various types of tea leaves, and of being subjected to extraction --
Line 11, delete "Namely, the", insert -- The --
Line 13, delete "O", insert -- 0 --
Line 22, delete "and to be extracted"
Line 23, delete "water,", insert -- water --
Line 26, delete "comprises", insert -- comprise --
Line 27, delete "has", insert -- have --
Line 45, delete "optimum", insert -- optimal --
Line 46, delete "principle", insert -- principal --
Line 61, delete "exhibit", insert -- exhibits --

UNITED STATES PATENT AND TRADEMARK OFFICE
CERTIFICATE OF CORRECTION

PATENT NO. : 6,742,660 B2
DATED : June 1, 2004
INVENTOR(S) : Suzuki et al.

It is certified that error appears in the above-identified patent and that said Letters Patent is hereby corrected as shown below:

Column 4,
Line 4, delete "exhibit", insert -- exhibits --
Line 17, delete ".", insert -- : --
Line 38, delete "a", insert -- an --
Line 44, delete "polyhydronal", insert -- polyhedral --

Column 5,
Line 9, delete "from", insert -- forms --
Line 23, delete "to be"
Line 25, insert -- prevents --, before "the propagation"
Line 27, insert -- , --, after "and molds"
Line 33, delete "accelated", insert -- accelerated --
Line 39, delete "almost of", insert -- almost --
Line 59, delete "used or", insert -- used --

Column 6,
Line 55, delete "A comparative", insert -- Comparative --
Line 61, insert -- time --, after "at the same"

Column 7,
Line 4, delete "leaves", insert -- leaf --
Line 14, delete "were", insert -- was --
Line 15, after "method", insert -- ) --
Line 17, delete "was", insert -- were --
Line 28, after "fine", delete ","
Line 34, delete "pag", insert -- bag --
Line 37, delete "a bottom of", insert -- bottom of the --
Line 43, delete "the beaker was", insert -- the beaker were --

Column 8,
Line 13, delete "or more,", insert -- or more --
Table 2, delete "Before treatment", insert
    -- Before
       Treatment --
Table 3, delete "Before treatment", insert
    -- Before
       Treatment --

UNITED STATES PATENT AND TRADEMARK OFFICE
CERTIFICATE OF CORRECTION

PATENT NO. : 6,742,660 B2
DATED : June 1, 2004
INVENTOR(S) : Suzuki et al.

It is certified that error appears in the above-identified patent and that said Letters Patent is hereby corrected as shown below:

Column 8 (cont'd),
Table 4, delete "Before treatment", insert
-- Before
   Treatment --
Line 67, delete "bags were", insert -- bags was --

Column 9,
Line 8, delete "Pseudomonase areuginosa", insert -- Pseudomonas aeruginosa --
Table 5, delete "Pseudomonase areuginosa", insert -- Pseudomonas aeruginosa --
Table 6, delete "Pseudomonase areuginosa", insert -- Pseudomonas aeruginosa --

Column 10,
Line 16, delete "and but", insert -- but --
Line 19, delete "Particularly,", insert -- Particularly --
Line 22, delete "container,", insert -- container --
Line 35, delete "formed comprises", insert -- formed comprise --
Line 35, delete "principle", insert -- principal --
Line 36, delete "polyactate", insert -- polylactate --
Line 36, insert -- , -- after "1600 to 6400"
Line 39, delete "equation;" insert -- equation: --
Line 51, delete "portion of surfaces", insert -- portion of the surface --

Signed and Sealed this

Seventeenth Day of May, 2005

JON W. DUDAS
*Director of the United States Patent and Trademark Office*